United States Patent [19]

Barr

[11] Patent Number: 4,597,959
[45] Date of Patent: * Jul. 1, 1986

[54] SUSTAINED RELEASE BREATH FRESHENER, MOUTH AND PALATE COOLANT WAFER COMPOSITION AND METHOD OF USE

[76] Inventor: Arthur Barr, 2942 Shore Dr., Merrick, N.Y. 11566

[ * ] Notice: The portion of the term of this patent subsequent to Sep. 29, 1998 has been disclaimed.

[21] Appl. No.: 373,342

[22] Filed: Apr. 30, 1982

[51] Int. Cl.$^4$ .......................... A61K 9/26; A61K 9/50
[52] U.S. Cl. ........................................ 424/19; 424/20; 424/22; 424/49
[58] Field of Search ........................ 424/19, 20, 22, 49

[56] References Cited

U.S. PATENT DOCUMENTS

| | | | |
|---|---|---|---|
| 3,911,099 | 10/1975 | DeFoney et al. | 424/49 |
| 3,957,964 | 5/1976 | Grumm | 424/10 |
| 4,071,614 | 1/1978 | Grumm | 424/49 |
| 4,292,028 | 9/1981 | Barr | 424/19 |
| 4,329,333 | 5/1982 | Barr | 424/19 |

OTHER PUBLICATIONS

Fed. Register, Dec. 13, 1968, C.A. 46240(b); vol. 70, 1969.
Suzuki et al., C.A. 126190(x); vol. 88, 1978.

Primary Examiner—Donald B. Moyer
Assistant Examiner—C. Joseph Faraci
Attorney, Agent, or Firm—Roberts, Spiecens & Cohen

[57] ABSTRACT

A cosmetic breath freshener composition, in wafer form, having slow release comprising a multiplicity of microencapsulated liquid droplets of flavoring material contained in a base or carrier. The microcapsules are soluble in the saliva in the mouth to release the flavoring material at sustained rate. The base has an adhesive therein so that the formed wafer can be placed on the lower or upper gums of the user, thus being activated by the saliva in the mouth causing the capsules to release the flavoring material at a sustained rate for long periods of time in the mouth to mask bad breath and also offering a cool feel effect in the mouth of the user.

10 Claims, No Drawings

SUSTAINED RELEASE BREATH FRESHENER, MOUTH AND PALATE COOLANT WAFER COMPOSITION AND METHOD OF USE

FIELD OF THE INVENTION

The invention relates to a breath and mouth freshener composition capable of slow release, at a sustained rate, of a microencapsulated liquid flavoring material and to methods of use thereof.

The invention is particularly applicable to the use of such a breath freshener composition in a wafer form, for the general public but is also applicable for use by full or partial denture wearers.

The invention further relates to a method of delivery of breath and mouth freshener materials, medications, and caries retardants, at a sustained rate, of microencapsulated material and to methods of use thereof.

The invention is particularly applicable to the use of such materials in a self adhesive wafer form.

BACKGROUND

One of the major problems encountered by the general public is offensive breath, or "bad breath" due to food and beverage residues retained in the oral cavity producing this offensive cosmetic problem; in addition natural food odors, such as onions, garlic, etc. and the like add to "bad breath".

Up to this time no satisfactory compositions or methods have been obtained which will overcome these problems for long periods of time, and despite the widespread use of varying flavoring materials, there has been no effective long-lasting solution to overcome the problem of offensive breath (bad breath) with its accompanying bad mouth feel. Flavorings, such as spray breath fresheners, mouthwashes, chewing gum, lozenges, liquid drops and toothpaste as presently employed have only a limited life of very short duration and rapidly lose their ability to mask bad breath or offer long-lasting fresh, cool feel in the mouth.

SUMMARY OF THE INVENTION

An object of the invention is to provide a breath and mouth freshener composition and mouth coolant in a wafer form, having a slow release in the mouth, capable of eliminating offensive breath, and cooling the mouth.

A further object of the invention is to provide a wafer composition of minimum size, i.e. thickness and diameter so that placement of the wafer anywhere in the oral cavity would be comfortable while remaining in one position.

Yet another object of the invention is to provide a wafer composition which is self-dissolving in the mouth of the user so that when placed in the mouth the wafer will dissolve and there will not be any residue remaining for the user to discard.

A further object of the invention is to provide such a breath freshener composition, in a wafer form for use with full or partial dentures by compatability thereof with or without the use of a denture adhesive.

According to a feature of the invention, the breath and mouth freshener can be in the form of a wafer of minimum size, having an adhesive distributed therein for continuous adherent contact with the palate or gums of the user.

The invention also meets the oral gratification needs of the consumer by offering the additional benefits of a refreshlng taste and feel in the mouth; the feeling of the user being that of just having brushed the teeth.

In accordance with the invention, there is provided a breath freshener composition, in a wafer form, having slow release comprising a multiplicity of microencapsulated liquid droplets of flavoring materials the microencapsulated droplets being soluble in the saliva of the mouth to slowly release the flavoring materials when entering into contact with the saliva. As a consequence the microencapsulates can slowly release the liquid flavoring materials at a sustained rate. The microencapsulates are present in a wafer form which comprises a base of gelatin, gum arabic and/or Carrageenen with an adhesive distributed throughout. In this way the wafer can be applied to the gums and palate or the wafer can be directly applied to the inner or outer surfaces of full or partial dentures.

A further object of the invention is to provide a wafer containing a germicide having slow release in the oral cavity which will retard the growth of harmful bacteria, particularly after oral surgery when the risk of oral infection is high.

In a further aspect of the invention, the formation of caries, particularly in children is retarded by including stannous fluoride in the wafer in an amount of 1–5% by weight of the flavoring material.

In accordance with a specific embodiment of the invention, the encapsulated flavoring materials are present in an amount of 35–45% by weight of the composition. The base is present as a remainder of 55–65% and comprises a gum such as Gum Arabic (Acacia) and/or Carrageenan. The gum can be present in an amount of 10–40% by weight of the composition.

According to a further aspect of the invention, the base or carrier which may serve as an adhesive and/or binding agent for attachment to the gums of the user, is itself encapsulated and mixed with the microencapsulates of flavoring materials, in conjunction with the base material.

PRIOR ART

U.S. Pat. No. 2,701,212 relates to germicidal deodorizing powder adhesives and methods of manufacture thereof. The patent discloses powdered adhesives containing varlous amounts of finely divided karaya gum and borax with an without water-soluble chlorophyllin. This patent lacks any teaching concerning encapsulated minute droplets of flavoring material having slow release at a sustained rate.

U.S. Pat. No. 3,440,065 relates to an improved denture adhesive containing various additives, such as wood, flour, cellulose or other wood pulp derivatives which are added to a gum-petrolatum base. The patent discloses an adhesive composition of a topically acceptable hydrocolloid, powdered insoluble adsorptive cellulose material and petrolatum. The purpose of the cellulose material is to effect a greater hydration of the gum particles, not only on the surface, but throughout the paste and thereby effect a much stronger cohesive bond between the denture and the gingiva and palate. In addition, a flavoring oil is blended into the composition, but lacking is any teaching regarding sustained time release based on the use of encapsulated flavoring materials.

U.S. Pat. No. 3,886,265 discloses a mouth cleansing preparation containing at least one ene-diol compound having at most 6 carbon atoms and an oxidizing agent in the form of a water soluble peroxide. The composition is intended to eliminate bad breath and is employed in the form of a chewable tablet. The composition can contain flavoring agents, but these are not in the form of encapsulated droplets adapted for slow sustained release in the mouth.

U.S. Pat. No. 3,969,499 discloses dental adhesive materials in the form of plastic films or membranes which are implanted in or adhered to tissue, bone or tooth substrate in which a medicament such as a fluoride compound is imbedded. The medicament is released from the plastic over a period of time. Specifically, the composition is intended for use as a dental fissure sealant. There is no teaching in this reference of a sustained release of flavoring material.

U.S. Pat. No. 4,029,759 discloses a method for imparting a cooling property to a composition for use in the oral cavity. Specifically, the patent discloses the use of para-menthane derivatives to various substances used in the mouth, such as toothpaste, mouthwash, tooth powder, food stuffs and the like. The para-menthane derivatives can also be employed in combination with flavoring materials. Lacking in this disclosure is any teaching concerning sustained slow release of flavoring material in the mouth.

U.S. Pat. No. 4,071,614 discloses a dentifrice which contains encapsulated flavoring materials. The dentifrice contains two different flavoring materials in which one flavor is encapsulated in a thin walled capsule and the other is encapsulated in a thick walled capsule. The thin walled capsules rupture when the toothpaste is squeezed from the container and the thick walled capsules rupture in the course of brushing the teeth. The encapsulated material is not water-soluble and is intended for being broken by a mechanical action to release bursts of the flavoring material. There is thus no disclosure in respect of a slow sustained release of flavoring material, particularly, in conjunction with a static situation, such as, installation of dentures.

DESCRIPTION OF PREFERRED EMBODIMENTS

In order to confer a slow sustained release of flavoring materials into the mouth of the user there is employed a multiplicity of microencapsulated liquid droplets of flavoring material in a prepared base composition. The encapsulated droplets are soluble in the saliva in the mouth of the user so as to dissolve the microencapsulation material and release the flavoring material when entering into contact with the saliva in the mouth. It is noted that the entire wafer composition is dissolved without any remaining residue to be extracted by the user.

The formation of microencapsulated liquid droplets of material is well known in the art and does not form any part of the present invention. Hence, it will not be described at length herein. However, for the purpose of brief explanation, reference is made to the publication "Microencapsulation" by Herbig as presented in the "Encyclopedia of Chemical Technology" of Kirk-Othmer, Volume 13, 2nd Edition, pp. 436–456. As disclosed herein, minute particles or liquid droplets of material can be encased by an impervious capsule wall and isolated from the surrounding atmosphere.

In the circumstances of the present invention, the encapsulate liquid flavoring material can be spray dried or encapsulated in a non-water soluble coating and the coating may be of varying wall thicknesses in order to provide for sustained release of the flavoring material over a period of time, of the order of several hours, when the encapsulated droplets come into contact with saliva in the mouth. The encapsulating material must satisfy the purposes of the invention of being saliva-soluble and providing sustained release of the encapsulated flavoring material while being not soluble in water and thus capable of long shelf life without weight loss to the ambient atmosphere. Furthermore, because of this property, breakdown of capsules will not be speeded up by the intake of drinking water or other water containing beverages.

The multiplicity of microencapsulated liquid droplets of flavoring materials is incorporated into a base formed as a wafer having adhesive therein wherein the wafer can be affixed to the palate or gums of the wearer and slowly release the flavoring material. The wafer can thus be utilized whether the user wears dentures or not and will provide protection against "bad breath" for several hours.

The microencapsulated liquid droplets are composed of liquid flavoring material constituting 85–95% by weight of the microcapsules and 5–15% by weight of encapsulating wall material consisting essentially of cross-linked gelatin. The wall material comprises gelatin, an adhesive binder such as gum arabic, a gelatin cross-linking agent such as glutaraldehyde and sodium silicate. The gelatin and binder are present in equal amounts of between 2.25 and 7.25% and the cross-linking agent and sodium silicate are present in equal amounts of 0.25%.

The flavoring material can be of wide range and by way of example, it may be a mint flavor such as spearmint, peppermint, oil of wintergreen, etc. Also usable are fruit flavors or other flavorings such as vanillin, menthol, eucalyputus oil or combinations of flavorings. The microeapsules containing the flavoring material are present in an amount of 35–45% by weight of the composition.

The base which represents the remainder of the composition is present in an amount of 55–65% by weight and serves as the vehicle for containing the encapsulated material distributed therethroughout to form the wafers.

The base or carrier and the encapsulated flavoring material are formed as a slurry and are utilized to produce wafers or tablets in conventional manner in a tabletting machine extruder, spray or mold apparatus. The slurry may contain various thickening agents, such as 10% by weight Klucil, or 10% by weight Carrageenan, or 40% by weight Gum Arabic. The viscosity range of the slurry is 2200–3000cps Brookfield at 20° C.

The base or carrier can contain additional substances and these include a small percentage of the order of 0.3 to 1% of methyl and propyl parabens as an antifungicide, 0.3–1% Benzocaine as an analgesic and a small percentage of the order of 0.5–01% of a natural liquid sweetener such as Pharma-Sweet.

EXAMPLE I

Microencapsulated droplets were prepared by encapsulating peppermint flavoring in liquid droplet form in an encapsulating material which is substantially not soluble in water but is soluble in saliva in the mouth of the user.

A microencapsulated droplet composition prepared according to the invention includes the following components in % by weight.

| | |
|---|---|
| liquid peppermint | 85% |
| gelatin | 7.25% |
| gum arabic (acacia) | 7.25% |
| glutaraldhyde (gelatin a cross-linking agent) | .25% |
| sodium silicate (Aerosil 972) | .25% |

The microencapsulated droplets have a size of between 10 and 400 microns and a wall thickness of less than 5 microns and generally between 2 and 3 microns. The droplets were found to have a maximum weight loss in air of about 10% which was achieved within 9 days whereafter there was no further weight loss. The microencapsulated droplets were not soluble in water but were slowly soluble in the saliva in the mouth of the user.

The following composition of the invention was prepared in wafer form by the method to be described hereafter.

| INGREDIENTS | PERCENT BY WEIGHT |
|---|---|
| Microencapsulated peppermint droplets (as prepared above) | 20 |
| Water | 39.4 |
| Gum Arabic | 40 |
| Propylparaben | 0.3 |
| Benzocaine (Ethyl aminobenzoate) | 0.3 |

The same composition as described above was prepared without the presence of the ethyl aminobenzoate in one case and without the propylparaben in another case. In each case the amount of water was increased by 0.3% by weight to make up the absence of the respective ingredient.

EXAMPLE II

The same procedure in Example I was carried out using Carrageenan and Klucel in amounts of 10% by weight instead of Gum Arabic in an amount of 40% by weight (the balance being made up by the addition of 30% by weight of water) with substantially the same results.

The composition was prepared by adding irradiated tap water to a stainless steel kettle and then adding the propylparaben and Benzocaine. The mixture was then heated to a temperature of 20° C.

The gum Arabic was then added and mixing was continued until a uniform mixture was obtained. The encapsulated flavoring was then added and mixing was continued making sure that the viscosity is between 2200 to 3000 centipoises and that the mixer clearances are proper so as to not rupture the microcapsules. The natural sweetener may be added at this time. After about 10 minutes mixing the breath freshener slurry was transferred to suitable drums for storage and cooling to ambient temperature. The material was then formed into round wafers, each ⅛" to ½" in diameter and approximately, 1/32" to ⅛" in thickness.

In use, the wafer applied to the upper or lower gums adjacent to the cheek, was found to provide effective protection against bad breath for periods of time in the order of 4–6 hours.

It was also found that the wafer composition had a cooling effect in the mouth of the user, akin to the feeling of having just brushed the teeth. It was also found that the cooling effect and the sustained release of the flavoring material tends to suppress the desire to smoke and to inhibit the desire for snacks.

The same procedure in Example II was carried out with the addition of 1.4% by weight of phenol to the flavoring material. Similar germicides such as Hyamin No. 10X, may be used without the flavoring material, but they must be non-soluble in water or blended with a carrier that is non-soluble in water. Clove oil may be used because of its germicidal and flavoring properties.

It was found that the sustained release of a germicide in the oral cavity greatly reduces the pathogens in the mouth and greatly reduces the risk of infection immediately after extractions and for periods up to 5 to 6 hours. This may preclude the necessity of the patient taking an antibiotic for the same purpose, particularly if a patient is allergic to certain antibiotics or has developed an immunity to them.

The same procedure as in Example 11 was carried out with the addition of stannous fluoride to the flavoring material of amounts between 1 and 5%. This provided sustained release in the mouth of a proven retardant of caries, over a longer duration of time than that consumed by brushing the teeth with conventional tooth paste containing stannous fluoride, sodium fluoride, sodium monofluororphosphate. The combination of a sustained release breath freshener and caries retardant was deemed to be unique and highly beneficial to the public at large.

Although the invention has been described in conjunction with the specific embodiments thereof it will be apparent to those skilled in the art that numerous modifications and variations can be undertaken without departing from the scope and spirit of the invention as defined in the attached claims.

What is claimed is:

1. A method of releasing a flavoring material and providing effective protection against bad breath in the mouth of a user, said method comprising forming a wafer composition consisting of microencapsulated droplets of liquid flavoring material in a base or carrier, said microencapsulated droplets having a coating which is substantially non-soluble in water but which is soluble in the saliva of the mouth, said wafer having adhesive therein such that when the wafer is placed at any convenient place on the palate or on the upper or lower gums, adjacent to the cheek of the user, thereafter the saliva in the mouth causes the adhesive therein to adhere to the gum and at the same time the flavoring material is slowly released, at a sustained rate, in situ in the mouth as the droplets of material are slowly dissolved, thereby to offer effective relief against bad breath, for periods of time in the order of 4–6 hours, said microencapsulated droplets being present in an amount of 35–45% by weight and consisting essentially of liquid flavoring material in an amount of 85–95%, and an encapsulating wall material of cross-linked gelatin in an amount of 5–15% by weight, said base or carrier consisting essentially of an adhesive.

2. A method as claimed in claim 1 wherein said microencapsulated droplets consist of the following in percent by weight:

| | |
|---|---|
| Liquid flavoring material | 85% |
| Gelatin | 7.25% |
| Gum Arabic | 7.25% |
| Glutaraldhyde | .25% |

| -continued | |
|---|---|
| Sodium Silicate | .25%. |

3. A method as claimed in claim 2 wherein said microencapsulates are added to said base or carrier to form a slurry from which wafers are formed.

4. A method as claimed in claim 3 wherein said base or carrier includes an anti-fungicide, or an analgesic or combinations thereof.

5. A method as claimed in claim 4 wherein said antifungicide is an alkylparaben and said analgesic is ethylaminobenzoate.

6. A method as claimed in claim 3 wherein said base or carrier to which the microcapsulates are added consists essentially of in percent by weight:

| microcapsulates | 20% |
|---|---|
| water | 39.4% |
| gum arabic | 40% |
| propylparaben | 0.3% |
| ethyl aminobenzoate | 0.3%. |

7. A method as claimed in claim 3 wherein said base or carrier to which the microcapsulates are added consists essentially of in percent by weight:

| microcapsulates | 20% |
|---|---|
| water | 69.7% |
| Carrageenan or Klucel | 10% |
| propylparaben | 0.3%. |

8. A method as claimed in claim 1 wherein the flavoring material is a mint material.

9. A method as claimed in claim 1 wherein said flavoring material comprises a germacide.

10. A method as claimed in claim 1 wherein said flavoring material comprises stannous fluoride.

* * * * *